United States Patent
Popper

(10) Patent No.: US 6,397,678 B1
(45) Date of Patent: Jun. 4, 2002

(54) METHOD AND APPARATUS FOR MEASURING OBJECTS, PARTICULARLY USEFUL FOR MEASURING DIAMONDS

(75) Inventor: Shay Popper, 11 Yasmin Street, 42 823 Tzuran (IL)

(73) Assignees: Shay Popper, Tzuran; Kibbutz Ramat Rachel, Kibbutz Ramat Rachel, both of (IL)

( * ) Notice: Subject to any disclaimer, the term of this patent is extended or adjusted under 35 U.S.C. 154(b) by 0 days.

(21) Appl. No.: 09/848,302

(22) Filed: May 4, 2001

(51) Int. Cl.[7] ............................................. G01N 29/12
(52) U.S. Cl. ........................... 73/580; 73/579; 73/661; 209/592
(58) Field of Search ................ 73/579, 580, 432.1, 73/864.31, DIG. 1, 661; 209/592, 593, 643, 645, 919

(56) References Cited

U.S. PATENT DOCUMENTS

| | | | | |
|---|---|---|---|---|
| 5,046,362 A | * | 9/1991 | Strubbe | 73/579 |
| 5,140,857 A | * | 8/1992 | Reid | 73/573 |
| 5,813,280 A | * | 9/1998 | Johnson et al. | 73/643 |
| 5,850,370 A | * | 12/1998 | Stringer et al. | 367/128 |
| 5,869,763 A | * | 2/1999 | Vig et al. | 73/580 |
| 6,064,629 A | * | 5/2000 | Stringer et al. | 367/99 |
| 6,146,268 A | * | 11/2000 | Behnke et al. | 73/643 |
| 6,260,408 B1 | * | 7/2001 | Vig et al. | 73/64.53 |
| 6,298,009 B1 | * | 10/2001 | Stringer | 367/99 |

* cited by examiner

Primary Examiner—Hezron Williams
Assistant Examiner—Jacques Saint-Surin
(74) Attorney, Agent, or Firm—G. E. Ehrlich Ltd.

(57) ABSTRACT

A method and apparatus for measuring the mass of individual objects, particularly small diamonds, within a predetermined range of sizes, by conveying the objects towards an oscillatable probe having a predetermined mass and a vacuum port of smaller dimensions than those of the objects; applying vacuum to the vacuum port to attract and hold thereto one of the individual objects to thereby add its mass to the mass of the oscillatable probe; measuring the oscillating frequency of the oscillatable probe while the individual object attracted thereto is held by the vacuum applied to the vacuum port, and utilizing the measured oscillating frequency of the probe and the object attracted thereto to compute the mass of the object, before releasing the vacuum to release the object.

31 Claims, 5 Drawing Sheets

METHOD AND APPARATUS FOR MEASURING OBJECTS, PARTICULARLY USEFUL FOR MEASURING DIAMONDS

FIELD AND BACKGROUND OF THE INVENTION

The present invention relates to a method and apparatus for measuring the mass, or weight, of individual objects. The invention is particularly useful for measuring the mass or weight of diamonds or other precious or semi-precious stones, especially the smaller diamonds, e.g. of up to about 1 carat (100 points), and the invention is therefore described below with respect to this application.

Since the value of a diamond or other precious stone depends to a high degree on its carat weight, it is important to measure the weight of the stones as accurately as possible. One traditional way of doing this is by the use of scales or pan balances. However, such traditional methods are time-consuming, and are therefore not practical with very small stones, such as stones of up to about 50 points (00.50 carats). Such small stones are therefore generally sold in the form of parcels, e.g. a parcel of 1000 stones, of 35 points average. However, since the value of stones increases inordinately with its size, it will be appreciated that sorting even such parcels of stones into groups more precisely representing their actual weight, would greatly add to the overall value of the respective parcel of stones.

Sieves or hole gauges are also used for sorting large quantities of small polished stones, e.g. less than 100 points. Such sieves or hole gauges generally include a steel plate with a grid of accurate holes according to the size of the stones to be sorted. While such sieves and hole gauges permit sorting large numbers of small stones, each group produced by their use includes a relatively large range of stone weights.

At the present time, therefore, there is a critical need for measuring the weight of small objects in general, and small diamonds or other precious stones in particular, at a relatively high rate and with a relatively high degree of accuracy.

OBJECTS AND BRIEF SUMMARY OF THE INVENTION

One object of the present invention is to provide a novel method and apparatus for measuring the mass and/or weight of individual objects capable of being implemented at a high rate and with a high degree of accuracy in such measurements. Another object of the invention is to provide such a method and apparatus particularly useful for measuring the weight of small diamonds or other precious stones.

According to one aspect of the present invention, there is provided a method of measuring the mass of individual objects, comprising: conveying the objects towards an oscillatable probe having a predetermined mass and a vacuum port of smaller dimensions than those of the objects; applying vacuum to the vacuum port so as to attract and hold thereto one of the individual objects to thereby add its mass to the mass of the oscillatable probe; measuring the oscillating frequency of the oscillatable probe while the individual object attracted thereto is held by the vacuum applied to the vacuum port; utilizing the measured oscillating frequency of the probe and the object attract thereto to compute the mass of the object; and releasing the vacuum to release the object from the vacuum port preparatory for using the probe to measure the mass of another one of the individual objects.

According to further features in the preferred embodiments of the invention described below, the vacuum port has a mouth of conical configuration of larger dimensions than the objects.

According to further features in the described preferred embodiments, the probe includes a piezoelectric device. In one described preferred embodiment, the piezoelectric device generates an electrical output by the impact of the object when attracted to the vacuum port, which electrical output is at the oscillating frequency measured and utilized to compute the mass of the individual object. In another described embodiment, the piezoelectric device is driven at a first frequency which frequency is changed by the mass of the object when attracted to the vacuum port, the change in frequency being measured and utilized to compute the mass of the individual objects attracted to the vacuum port.

According to further features in the described preferred embodiments, the oscillating frequency of the probe is measured after a predetermined time delay following the contact of the object with the vacuum port.

According to further features in one described preferred embodiment, the probe overlies the objects such that the objects are moved against gravity towards the vacuum port by the vacuum at the vacuum port.

In another described embodiment, the probe underlies the objects such that the objects are moved with gravity(rather than against) gravity towards the vacuum port by the vacuum at the vacuum port.

According to another aspect of the present invention, there is provided apparatus for measuring the mass of individual objects within a predetermined range of sizes, comprising: an oscillatable probe having a predetermined mass and a vacuum port of smaller dimensions than those of the objects; a conveyor for conveying the individual objects towards the probe; a vacuum source for applying vacuum to the vacuum port of the probe so as to attract and hold thereto one of the individual objects to thereby add its mass to the mass of the probe; and an electrical measuring system for measuring the oscillating frequency of the probe while the object attracted to its vacuum port is held thereto by the vacuum at the vacuum port, and for utilizing the measured frequency of the probe and object to compute the mass of the object.

As will be described more particularly below, the method and apparatus constructed in accordance with the foregoing features are particularly useful for measuring the mass or weight of small diamonds or other precious stones, such as diamonds of less than 100 points (1 carat).

Further features and advantages of the invention will be apparent from the description below.

BRIEF DESCRIPTION OF THE DRAWINGS

The invention is herein described, by way of example only, with reference to the accompany drawings, wherein.

DESCRIPTION OF PREFERRED EMBODIMENTS

Figure 1:
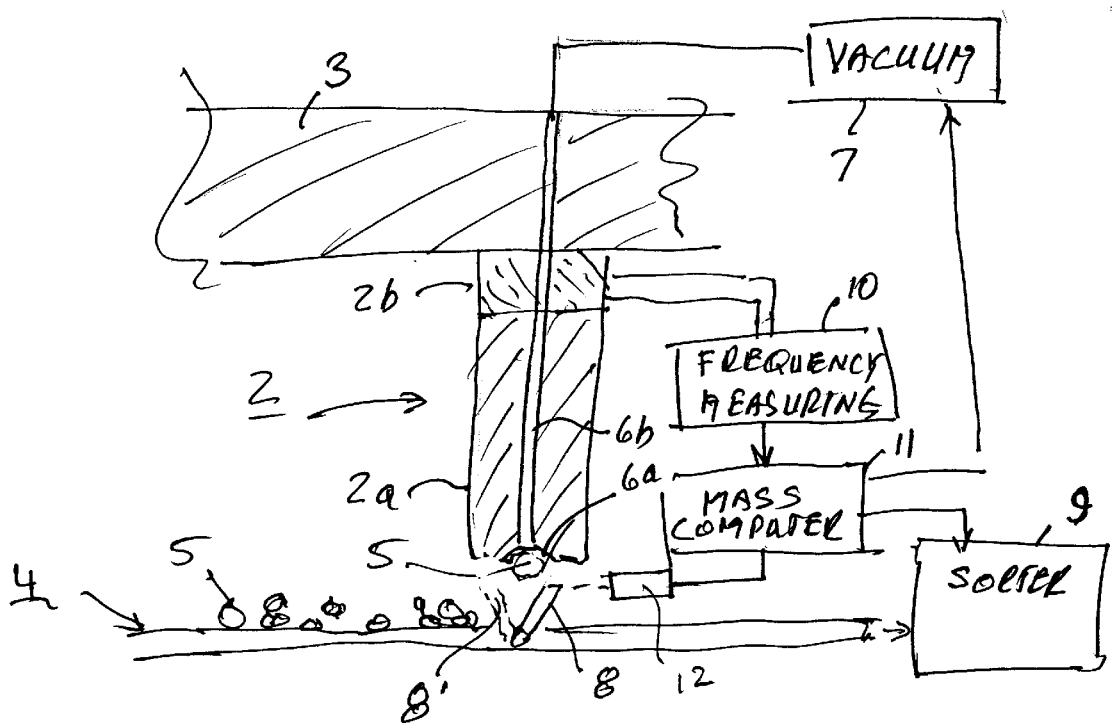
FIG. 1 illustrates one form of apparatus constructed in accordance with the present invention particularly useful for measuring the mass or weight of small diamonds (or other precious stones) in a relatively quick and precise manner.
Figure 2:
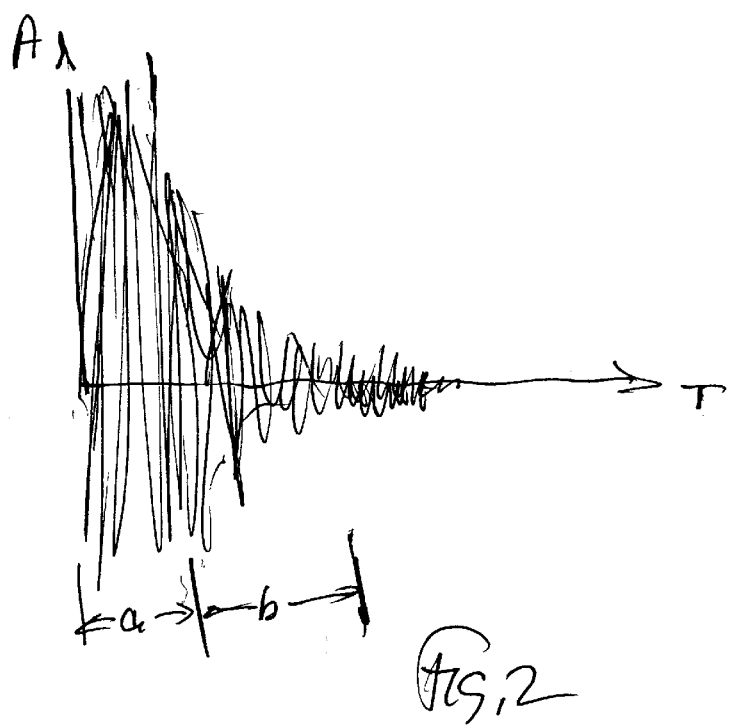
FIG. 2 illustrates an example of the electrical signal produced by the use of the device of FIG. 1.

References is first made to FIG. 1 illustrating one form of apparatus constructed in accordance with the present invention particularly useful for measuring the mass or weight of small diamonds or other precious or semi-precious stones with high precision (e.g. to a point or fraction of a point), and at a relatively rapid rate (e.g. several per second).

The apparatus illustrated in FIG. 1 includes a probe, generally designated 2, mounted by a mounting member 3 over a conveyor 4 for conveying the individual objects, in this case small polished diamonds or other precious stones, whose mass or weight is to be measured. Probe 2 includes a vacuum port, shown at 6, overlying the conveyor 4 and connected to a vacuum source 7, so as to attract and hold by vacuum an individual stone as it is conveyed by conveyor 5.

As shown in FIG. 1, each stone 5 is directed to the vacuum port 6 by a deflector 8 before it is weighed in a manner to be described below; and after it has been weighed, deflector 8 is actuated to the position illustrated at 8' in FIG. 1 to direct the stone from the probe 2 back to the conveyor 4 or to another conveyor for conveying the stone to a sorter 9 sorting the stones according to their weights. Deflector 8 can be omitted, but if provided, it should not, of course, contact the probe.

Vacuum port 6 is of smaller size than the range of sizes to be weighed and sorted. Accordingly, the attraction of a stone 5 towards the vacuum port 6 will cause the stone to impact against the probe 2 and to be held thereto by the vacuum. This impact of the stone causes the probe to oscillate at a frequency corresponding to the mass of the probe together with the mass of the stone 5 held at its vacuum port 6.

Probe 2 includes a cylindrical iron section 2a of large mass formed with the vacuum port 6 impacted by the stone 5 to produce the oscillations in the probe. Probe 2 further includes a piezoelectric device 2b between its iron section 2a and its mounting 3. Piezoelectric device 2b senses the mechanical oscillations produced by the impact of the stone 5 and generates an output signal which is applied to a frequency measuring circuit 10.

The output signal produced by piezoelectric device 2b thus corresponds to the frequency of oscillations produced in probe 2 by the impact of the stone 5. This oscillation frequency is a function of the total mass of the probe, i.e. the mass of its iron section 2a and its piezoelectric device 2b together with the mass of the stone 5 held in the vacuum port 6. Since the mass of the iron section 2a of the probe, as well as the mass of the piezoelectric device 2b, can be precisely measured, and since the frequency of a signal can also be precisely measured, it is possible to compute the mass of the stone 5 with a high degree of precision from the output signal of the piezoelectric device 2b.

Computer 11 receives the output from the frequency measuring circuit 10 and computes the mass of the stone 5 attracted to the vacuum port 6. When this computation is completed, computer 11 controls an actuator 12, which actuates deflector 8 (if provided) to its broken-line position 8' illustrated in FIG. 1. Computer 11 also controls vacuum source 7 to interrupt the vacuum supplied to the vacuum port 6, so as to permit the stone 5 to drop back to the conveyor 4 and to be conveyed to the sorter 9. Computer 11 additionally controls the sorter 9 to sort the stone according to its computed weight.

Many types of sorters may be used for this purpose, for example the leaf-type sorters commonly used for sorting mail, checks and other objects at a rapid rate to a plurality of compartments.

The face of the iron section 2a formed with the vacuum port 6 is of conical configuration, as shown at 6a, to define a mouth of larger dimensions than the stones 5, and thereby to guide the attracted stone 5 to the vacuum port 6. The stone is held to the vacuum port 6 by the vacuum produced from source 7. This vacuum is communicated to the vacuum port via vacuum passageway 6b through the mounting member 3, piezoelectric device 2b, and the iron section 2a of the probe 2. When the vacuum source is interrupted, the stone falls by gravity back to the conveyor 4.

As described above, the impact of the stone 5 against the probe 2, produces oscillations in the probe which are sensed by piezoelectric device 2b to produce an output signal of a frequency corresponding to the total mass of the probe with the stone 5 attracted thereto. It has been found that more accurate results are obtainable when the measurement of the output frequency of the piezoelectric device is delayed for a predetermined time interval following the impact of the stone. Best results were produced when this delay interval was from 5–15 $\mu$s, preferably about 10 $\mu$s; and when the frequency measuring interval following the delay was for about another 10–30 $\mu$s, preferably 10$\mu$.

Figure 3:
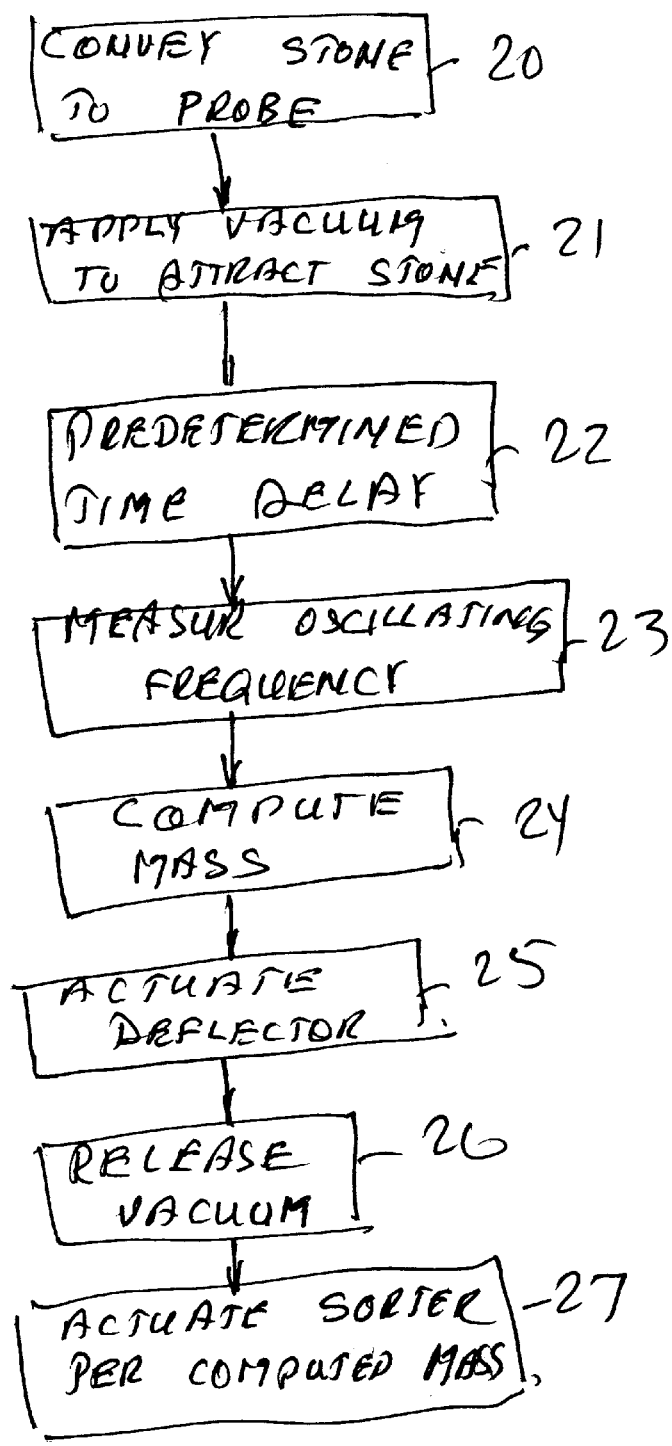
FIG. 3 is a flowchart illustrating a preferred method of using the device of FIG. 1 for measuring the mass or weight of small diamonds.

FIG. 3 is a flowchart illustrating the operation of the apparatus of FIG. 1 as described above. As a stone is conveyed to the oscillating probe 2 (block 20) the vacuum source 7 is actuated to apply vacuum to the vacuum port 6 and thereby to attract a stone thereto with an impact (block 21). After a predetermined time delay, e.g. about 10 $\mu$s (block 22), the output frequency from the piezoelectric device 2b is measured by the frequency measuring circuit 10 (block 23). This measurement is used by the computer 11 to compute the mass of the impacted stone 5 (block 24).

When this computation has been completed, computer 11 actuates deflector 8 (if provided) to its broken-position 8' in FIG. 1, and interrupts the vacuum from the vacuum source 7. The stone is thus released (block 26) and falls by gravity back onto the conveyor 4 or another conveyor. Computer 11 also actuates the sorter 9 to direct the stone to the appropriate compartment as determined by the measured mass (block 27).

The mass of the mounting member 3 should be much larger, by several orders of magnitude, than the mass of the probe 2, including the iron section 2a and the piezoelectric device 2b, so as not to be oscillated by the impact of the stone, and thereby not affect the oscillation frequency produced by this impact.

Figure 4:
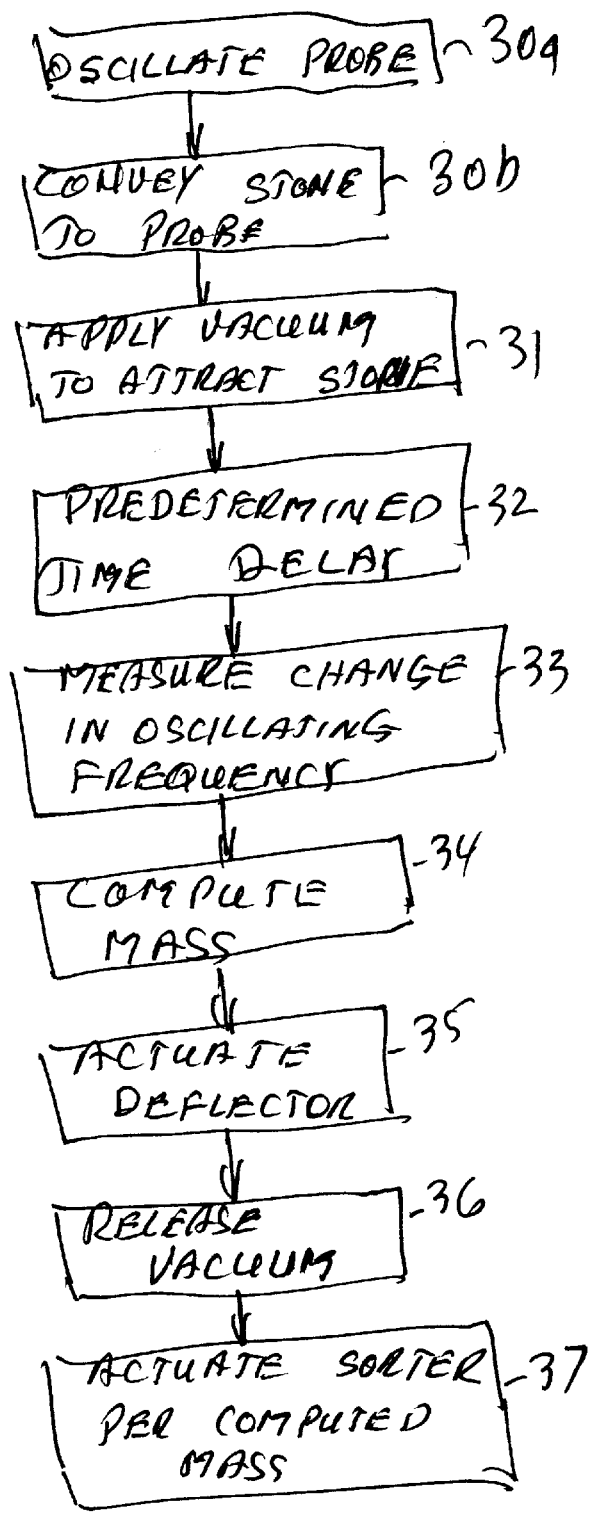
FIG. 4 is a flowchart illustrating an alternative method of using the apparatus of FIG. 1 for measuring the mass or weight of small diamonds.

In the method described above with respect to FIG. 3, the piezoelectric device 2b is used as a passive device, to merely generate the oscillations produced in the probe 2 by the impact of the stone 5. FIG. 4 illustrates a variation wherein the piezoelectric device 2b is used as an active device, in that it is electrically powered to drive the probe 2 to produce oscillations at the drive frequency.

Thus, as shown in FIG. 4, the piezoelectric device 2b is driven at a predetermined frequency (block 30a) while the stone is conveyed to the oscillating probe (block 30b). As in the flowchart of FIG. 3, the vacuum is applied to the vacuum port to attract and hold the stone thereto (block 31) After a predetermined time delay (block 32), the frequency, or the change in frequency, of the output signal from the piezoelectric device 2b is measured (block 23) and is utilized to measure the mass of the stone (block 24).

Thus, in this variation, although the piezoelectric device is separately driven by a power supply, its oscillating frequency, after the stone has been attracted to the probe, also depends on the total mass of the probe, and thereby enables a determination to be made of the mass of the stone itself.

After the mass of the attracted stone has been computed (block 34), the computer actuates the deflector (block 35), releases the vacuum (block 36), and actuates the sorter (block 37) in the same manner as described above with respect to blocks 24, 25, 26 and 27, respectively in FIG. 3.

Figure 5:
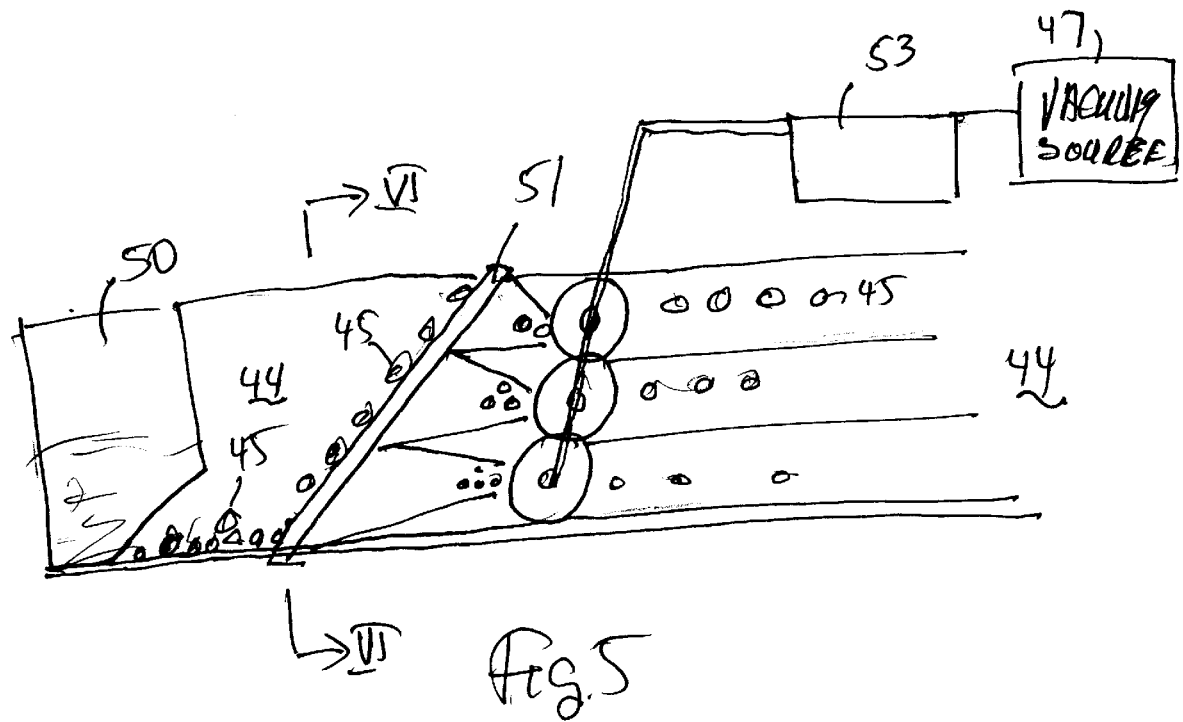
FIG. 5 is a plan view illustrating a more comprehensive apparatus constructed in accordance with the present invention and also capable of sorting the objects (e.g. small diamonds) according to their weights.
Figure 6:
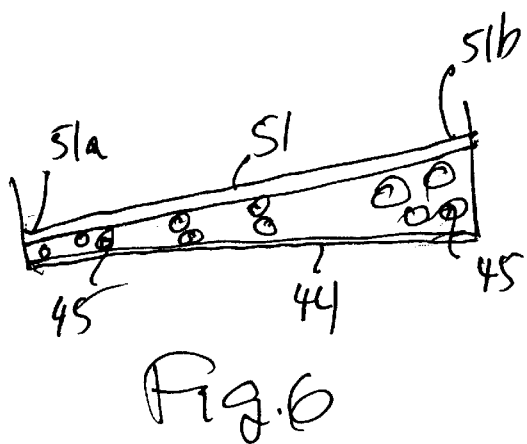
FIG. 6 is a transverse view along line VI—VI of FIG. 5.

FIGS. 5 and 6 illustrate another apparatus constructed in accordance with the present invention. The apparatus illustrated in FIGS. 5 and 6 includes a plurality of probes, therein designated 42a–42n, overlying the conveyor 44 for conveying the stones 45 to be weighed and sorted. Each probe 42a–42n may be constructed as described above with respect to FIG. 1, to include a vacuum port (shown in broken lines 46 in FIG. 5), communicating with a vacuum source 47, so as to attract and hold one of the stones 45 as these stones are conveyed by conveyor 44.

In the apparatus of FIGS. 5 and 6, however, the stones are first sorted to different size groups before reaching the probes 42a–42n. Thus, as shown in FIG. 5, the stones are fed from a hopper 50 by the conveyor 44 under an inclined sorter bar 51 overlying the conveyor 44. The side 51a of sorter bar 51 aligned with the outlet of the hopper 50 is at the lowest elevation over the conveyor 44, and the opposite side of the bar 51b is at the highest elevation. Sorter bar 51 is slanted in the direction of movement of the conveyor 44 so that the smaller sized stones are permitted to clear the bar 51 at the low-elevation side 51a, whereas the larger stones move along the bar and can clear the bar only at the highest-elevation side 51b.

As shown in FIG. 5, downstream of the sorter bar 45 are a plurality of guides 52a–52n, one for guiding the stones clearing the sorter bar to their respective probes 42a–42n. Thus, each probe, weighs its respective stone, and then releases the stone in the manner described above back to the conveyor 44, which conveys the stone to the respective sorter compartment.

As further shown in FIG. 5, vacuum source 47 is connected to the vacuum ports 46 of all the probes 42a–42n via a trap 53. Trap 53 collects any small particles (e.g. dirt, diamond dust, or the like) of such small dimensions that they pass through the probes towards the vacuum source.

Figure 7:
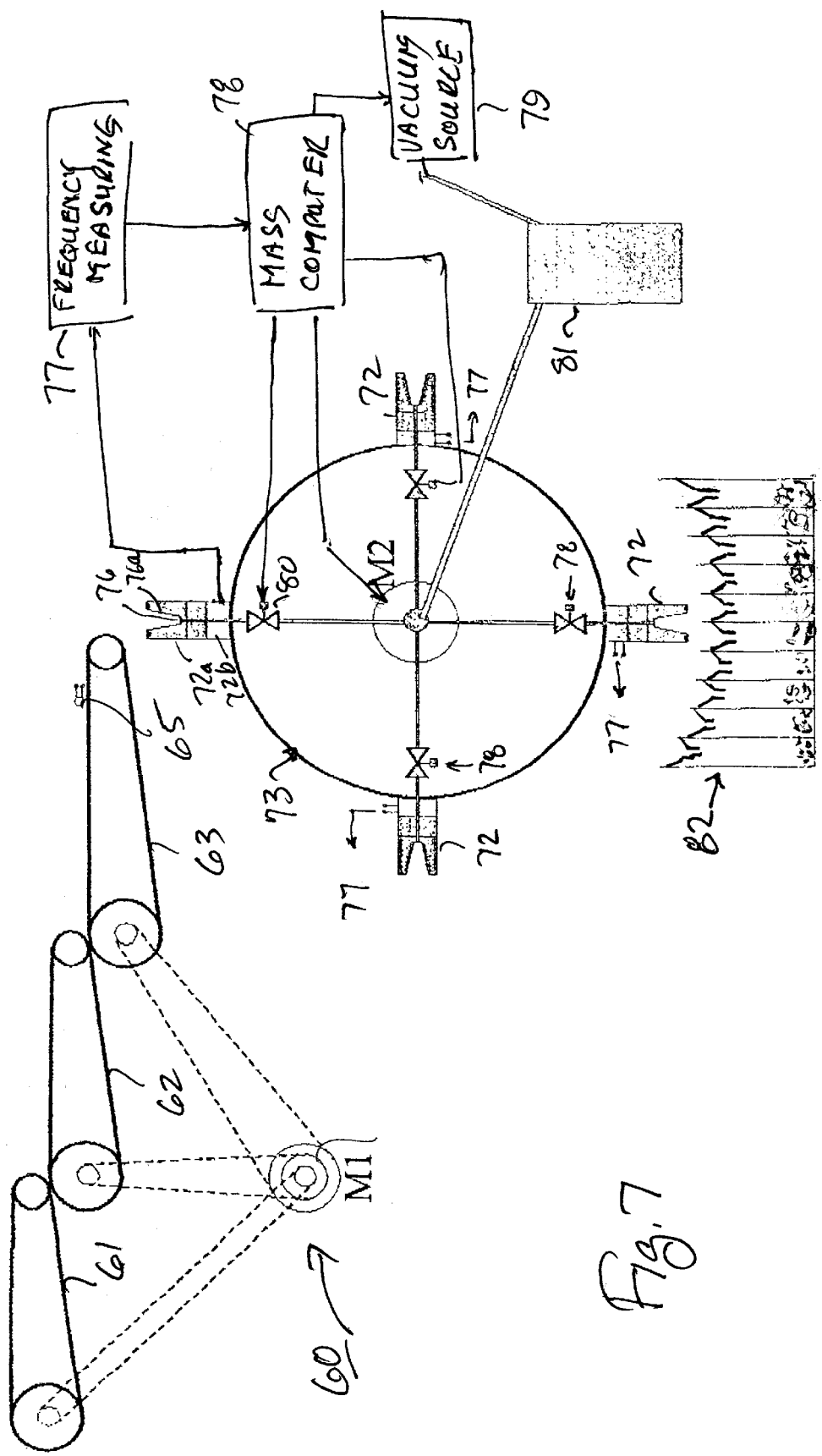
FIG. 7. Illustrates another apparatus constructed in accordance with the present invention for weighing small diamonds and for sorting them according to their weights.

FIG. 7 illustrates another form of apparatus constructed in accordance with the present invention wherein the probes are mounted, not above the stone conveyor as described above, but rather below the stone conveyor. In addition, the probes are mounted on a movable carriage, in the form of a rotatable transfer table, which transfers each stone, after having been weighed, to its appropriate sorting cell, according to its respective weight.

Thus, as shown in FIG. 7, the conveyor, generally designated 60, includes a plurality of conveyor belts 61, 62, 63 all driven by a drive M1, for conveying the stones 65 to a location overlying the probes which determine their respective weights. In the apparatus illustrated in FIG. 7, there are four probes, generally designated 72, mounted around the circumference of a transfer table 73. Each probe 72 is generally of the same construction as probe 2 in FIG. 1. Thus, each includes a vacuum port 76 having a mouth 76a for receiving a stone 65 when dropped thereon; a heavy iron section 72a formed with the vacuum port 76; and a piezoelectric device 72b which is oscillated with the probe 72 by the impact of a stone 65 as described above with respect to FIG. 3, or which is separately driven but changes oscillation frequency when receiving such a stone 65 as described above with respect to FIG. 4.

The output of each probe is fed to a frequency measuring circuit 77 to measure the respective oscillating frequency, which is utilized by the computer 78 for determining the mass of the respective stone. Computer 78 also controls the drive M2 of the transfer table 73, the vacuum source 79, and valves 80 controlling the vacuum to the vacuum ports 76 of the probes 72. The vacuum system also includes a trap 81 for collecting small particles passing through the probes.

As shown in FIG. 7, the rotatable table 73 carrying the probes 72 overlies an assembly of sorting cells 82 which are traversed by each probe 72 as the table 73 rotates. Computer 78 controls the vacuum valves 80 to release the vacuum of each probe 72, as it traverses the sorting cells 82, at the proper instant to release the stone carried by the respective probe into the appropriate cell of the sorter 82 according to the computed weight of the stone.

It will thus be seen that, whereas in the arrangements described above with respect to FIGS. 1 and 5, each stone is attracted by vacuum to its probe against gravity, in the apparatus illustrated in FIG. 7, each stone is attracted by vacuum with gravity to its respective probe. While the probes in FIGS. 1 and 5 must therefore be located as close as possible to the conveyed stones without interference with their horizontal movements, this constraint is not present in the apparatus of FIG. 7.

While the invention has been described with respect to several preferred embodiments, it will be appreciated that these are said forth merely for purposes of example and that many variations and other applications of the invention may be made. For example, the apparatus can be operated without a vacuum and its output zeroized under such conditions, so that its readings during actual weighing operations will indicate the weight (or mass) of the stones. In addition, the described apparatus could be used for weighing and/or sorting other objects.

Many other variations and applications of the invention will be apparent.

What is claimed is:

1. A method of measuring the mass of individual objects within a predetermined range of sizes, comprising:

conveying said objects towards an oscillatable probe, having a predetermined mass and a vacuum port of smaller dimensions than those of said objects;

applying vacuum to said vacuum port to attract and hold thereto one of said individual objects to thereby add its mass to the mass of the oscillatable probe;

measuring for a predetermined time interval the oscillating frequency of said oscillatable probe while the individual object attracted thereto is held by the vacuum, applied to said vacuum port;

utilizing the measured oscillating frequency of the probe and said object attracted thereto to compute the mass of said object;

and releasing said vacuum to release said object from said vacuum port preparatory to using said probe to measure the mass of another one of said individual objects.

2. The method according to claim 1, wherein said vacuum port has a mouth of conical configuration of larger dimensions than said objects.

3. The method according to claim 1, wherein said probe includes a piezoelectric device.

4. The method according to claim 3, wherein said piezoelectric device generates an electrical output by the impact of the object against said probe when attracted to said vacuum port thereof, said electrical output being at the oscillating frequency measured and utilized to compute the mass of the individual object.

5. The method according to claim 3, wherein said piezoelectric device is driven at a first frequency, which frequency is changed by the mass of the object when attracted to said vacuum port, said change in frequency being measured and utilized to compute the mass of the individual object attracted to said vacuum port.

6. The method according to claim 1, wherein the oscillating frequency of said probe is measured after a predetermined time delay following the contact of the object with the vacuum port.

7. The method according to claim 6, wherein said predetermined time delay is about 5–20 $\mu$s.

8. The method according to claim 6, wherein the oscillating frequency of the probe is measured for a time interval of 10–30 $\mu$s, starting with a delay of 5–20 $\mu$s following the contact of the object with the vacuum port.

9. The method according to claim 1, wherein said probe overlies said objects such that each object is moved against gravity towards the vacuum port by the vacuum at the vacuum port.

10. The method according to claim 1, wherein said probe underlies said objects such that each object is moved with gravity towards the vacuum port by the vacuum at the vacuum port.

11. The method according to claim 1, wherein said individual objects are diamonds.

12. The method according to claim 11, wherein said diamonds are sorted to different size groups before being fed to said probe, there being one of said probes for each such size group to compute the mass of the diamonds in the respective size group.

13. The method according to claim 11, wherein said diamonds are sorted to different size groups after the mass of each has been computed by said probe and in accordance with the mass computed by the probe.

14. The method according to claim 13, wherein said probe is movably mounted under said conveyed diamonds such that each diamond is moved with gravity towards the vacuum port by the vacuum thereat, said probe being movable with the attracted diamond over a plurality of sorting compartments, the vacuum being released when the diamond held thereby overlies the sorting compartment corresponding to the mass of the measured diamond.

15. The method according to claim 14, wherein there are a plurality of said probes rotatably mounted on a transfer table underlying the conveyed diamonds.

16. Apparatus for measuring the mass of individual objects within a predetermined range of sizes, comprising;

an oscillatable probe having a predetermined mass and a vacuum port of smaller dimensions than those of said objects;

a conveyor for conveying said individual objects towards said probe;

a vacuum source for applying vacuum to said vacuum port of the probe so as to attract and hold thereto one of said individual objects to thereby add its mass to the mass of the probe;

and an electrical measuring system for measuring the oscillating frequency of the probe while the object attracted to its vacuum port is held thereto by the vacuum at the vacuum port, and for utilizing the measured frequency of the probe and object to compute the mass of the object.

17. The apparatus according to claim 16, wherein said vacuum port has a mouth of conical configuration of larger dimensions than said objects.

18. The apparatus according to claim 16, wherein said probe includes a piezoelectric device.

19. The apparatus, according to claim 16, wherein said piezoelectric device generates an electrical output by the impact of the object against said probe when attracted to said vacuum port thereof, said electrical output being the oscillating frequency measured and utilized to compute the mass of the individual object.

20. The apparatus according to claim 18, wherein said piezoelectric device is driven by an AC power supply at a power-supply frequency, which frequency is changed by the mass of the object when attracted to said vacuum port, said change in frequency being measured and utilized to compute the mass of the individual objects attracted to said vacuum port.

21. The apparatus according to claim 18, wherein said probe further includes a metal section formed with said vacuum port, said vacuum port being connected to said vacuum source by a passageway through said metal section and piezoelectric device.

22. The apparatus according to claim 21, wherein said metal section is of cylindrical configuration and has a mass substantially larger than said piezoelectric device.

23. The apparatus according to claim 16, wherein said electrical circuit measures the oscillating frequency, and utilizes said measured oscillating frequency for computing the mass of the object starting with a predetermined time delay after contact of the object with said vacuum port.

24. The apparatus according to claim 16, wherein said probe overlies said conveyor such that said objects are moved against gravity towards the vacuum port by the vacuum at said vacuum port.

25. The apparatus, according to claim 16, wherein the apparatus further includes a deflector movable from a first position to direct each object to the vacuum port of the probe, or to a second position, to direct the object, when released from the vacuum port, back to the conveyor for sorting according to the measured mass of the object.

26. The apparatus according to claim 16, wherein said apparatus includes a plurality of said probes, and said conveyor includes a sorter upstream of said plurality of probes for sorting the objects according to different size groups and for conveying the objects of each size groups to one of said probes.

27. The apparatus according to claim 26, wherein said sorter includes an inclined bar upstream of said plurality of probes for sorting the objects into groups according to their different sizes.

28. The apparatus according to claim 16, wherein said probe underlies said conveyor such that said objects are moved with gravity towards the vacuum port by the vacuum at said vacuum port.

29. The apparatus according to claim 28, wherein said probe is mounted on a movable carriage which is controlled to sort each object according to its mass.

30. The apparatus according to claim 29, wherein said movable carriage is a rotatable transfer table which traverses the inlets to a plurality of sorting compartments, said vacuum source being interrupted to release the vacuum at said vacuum port when the object thereat overlies a sorting compartment corresponding to the computed mass of said object.

31. The apparatus according to claim 30, wherein said rotatable transfer table mounts a plurality of said probes at different locations around the periphery of the transfer table.

* * * * *